(12) United States Patent
Sava Gallis et al.

(10) Patent No.: US 11,644,462 B2
(45) Date of Patent: May 9, 2023

(54) TARGETED NEAR-INFRARED IMAGING BY METAL-ORGANIC FRAMEWORKS

(71) Applicant: National Technology & Engineering Solutions of Sandia, LLC, Albuquerque, NM (US)

(72) Inventors: Dorina F. Sava Gallis, Albuquerque, NM (US); Kimberly Butler, Albuquerque, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 0 days.

(21) Appl. No.: 17/243,417

(22) Filed: Apr. 28, 2021

(65) Prior Publication Data

US 2021/0311041 A1   Oct. 7, 2021
US 2021/0311041 A1   Oct. 7, 2021

Related U.S. Application Data

(63) Continuation-in-part of application No. 15/994,904, filed on May 31, 2018, now Pat. No. 11,007,516.

(60) Provisional application No. 62/522,006, filed on Jun. 19, 2017.

(51) Int. Cl.
*G01N 33/543* (2006.01)
*G01N 33/544* (2006.01)

(52) U.S. Cl.
CPC ..... *G01N 33/54353* (2013.01); *G01N 33/544* (2013.01)

(58) Field of Classification Search
None
See application file for complete search history.

(56) References Cited

U.S. PATENT DOCUMENTS 9,920,076 B2   3/2018   Eddaoudi et al.
11,007,516 B1   5/2021   Sava Gallis et al.

OTHER PUBLICATIONS

Kukkar et al. AIP Conference Proceedings, 2018, 1-6.*
Luo et al. J. Am. Chem. Soc. 2017, 139, 9333-9340.*
Cao et al. ACS Sustainable Chem. Eng. 2016, 4, 6, 3586-3595.*
Yi et al. The Royal Society of Chemistry, 2016, 1-13.*
Lu, K. et al., "Nanoscale Metal-Organic Frameworks for Therapeutic, Imaging, and Sensing Applications," Advanced Materials, 2018, vol. 30, 1707634, 20 pages.

(Continued)

*Primary Examiner* — Clinton A Brooks
(74) *Attorney, Agent, or Firm* — Kevin W. Bieg

(57) ABSTRACT

Metal-organic frameworks (MOFs) comprising amines on the organic linker can be used for cell targeting. In particular, primary amine groups represent one of the most versatile chemical moieties for conjugation to biologically relevant molecules, including antibodies and enzymes. Different chemical conjugation schemes can be used to conjugate biological molecules to the amino functionality on the organic linker. For example, carbodiimide chemistry can be used to link a primary amine to available carboxyl groups on the protein. For example, sulfhydryl crosslinking chemistry can be used via Traut's reagent scheme. As a demonstration of the invention, the ability of EpCAM antibody-targeted MOFs to bind to a human epithelial cell line (A549), a common target for imaging studies, was confirmed with confocal microscopy.

12 Claims, 11 Drawing Sheets

(56) References Cited

OTHER PUBLICATIONS

Cai, W. et al., "Engineering Phototheranostic Nanoscale Metal-Organic Frameworks for Multimodal Imaging-Guided Cancer Therapy," ACS Applied Materials Interfaces, 2017, vol. 9, pp. 2040-2051.

Foucault-Collet, A. et al., "Lanthanide Near Infrafred Imaging in Living Cells with Yb3+ Nano Metal Organic Frameworks," Proceedings of the National Academy of Sciences, 2013, vol. 110, pp. 17199-17204.

Taylor-Pashow, K. M. L. et al., "Postsynthetic Modifications of Iron-Carboxylate Nanoscale Metal-Organic Frameworks for Imaging and Drug Delivery," Journal of American Chemical Society, 2009, vol. 131, pp. 14261-14263.

Liu, D. et al., "Phosphorescent Nanoscale Coordination Polymers as Contrast Agents for Optical Imaging," Angew. Chem. Int. Ed., 2011, vol. 50, pp. 3696-3700.

Nishiyabu, R. et al., "Nanoparticles of Adaptive Supramolecular Networks Self-Assembled from Nucleotides and Lanthanide Ions," Journal of American Chemical Society, 2009, vol. 131, pp. 2151-2158.

Miller, S. E. et al., "Metal-organic Frameworks as Biosensors for Luminescence-based Detection and Imaging," Interface Focus 6: 20160027, 14 pages.

Gao, X. et al., "In Situ Growth of Metal-Organic Frameworks (MOFs) on the Surface of other MOFs: A New Strategy for Constructing Magnetic Resonance/Optical Dual Mode Imaging Materials," Dalton Transanctions, 2017, vol. 46, pp. 13686-13689.

Rieter, W. J. et al., "Nanoscale Metal-Organic Frameworks as Potential Multimodal Contrast Enhancing Agents," Journal of American Chemical Society, 2006, vol. 128, pp. 9024-9025.

Wang, G. D. et al., "Gd and Eu Co-Doped Nanoscale Metal-Organic Framework as a $T_1$—$T_2$ Dual-Modal Contrast Agent for Magnetic Resonance Imaging," Tomography, 2016, vol. 2, pp. 179-187.

Sava-Gallis, D. F. et al., "Multifunctional, Tunable Metal-Organic Framework Materials Platform for Bioimaging Applications," ACS Applied Materials & Interfaces, 2017, vol. 9, 22268-22277.

Sava-Gallis, D. F. et al., "Biocompatible MOFs with High Absolute Quantum Yield for Bioimaging in the Second Near Infrared Window," CrystEngComm, 2018, vol. 20, pp. 5919-5924.

Kaslauskas, R., "Engineering more Stable Proteins," Chemical Society Review, 2018, vol. 47, pp. 9026-9045.

Le Basle, Y. et al., "Physicochemical Stability of Monoclonal Antibodies: A Review," Journal of Pharmaceutical Sciences, 2020, vol. 109, pp. 169-190.

Wang, S. et al., "Metal-Organic Framework Nanoparticles," Advanced Materials, 2018, vol. 30, 1800202, 14 pages.

Hu, Q. et al., "A Low Cytotoxic Cationic Metal-Organic Framework Carrier for Controllable Drug Release," Journal of Medicinal Chemistry, 2014, vol. 57, pp. 5679-5685.

Sava-Gallis, D. F. et al., "Antibacterial Countermeasures via Metal-Organic Framework-Supported Sustained Therapeutic Release," ACS Applied Materials & Interfaces, 2019, vol. 11, pp. 7782-7791.

Tamames-Tabar, C. et al., "Cytotoxicity of Nanoscaled Metal-Organic Frameworks," Journal of Materials Chemistry B, 2014, vol. 2, pp. 262-271.

Ling, P. et al., "Porphyrin Encapsulated Metal-Organics Frameworks as Mimetic Catalysts for Electrochemical DNA Sensing via Allsoteric Switch of Hairpin DNA," Analytical Chemistry, 2015, vol. 87, pp. 3957-3963.

Qi, X. et al., "Harnessing Surface-Functionalized Metal-Organic Frameworks for Selective Tumor Cell Capture," Chemistry of Materials, 2017, vol. 29, pp. 8052-8056.

Shih, Y-H. et al., "Trypsin-Immobilized Metal-Organic Framework as a Biocatalyst In Proteomics Analysis," ChemPlusChem, 2012, vol. 77, pp. 982-986.

Van Der Wel, C. et al., "Surfactant-free Colloidal Particles with Specific Binding Ability," Langmuir, 2017, vol. 33, pp. 9803-9810.

Durfee, P. N. et al., "Mesoporous Silica Nanoparticle-Supported Lipid Bilayers (Protocells) for Active Targeting and Delivery to Individual Leukemia Cells," ACS Nano, 2016, vol. 10, pp. 8325-8345.

Villegas, M. R. et al., "Multifunctional Protocells for Enhanced Penetration in 3D Extracellular Tumoral Matrices," Chemistry of Materials, 2018, vol. 30, pp. 112-120.

Butler, K. S. et al., "Antibody Targeted Metal-Organic Frameworks for Bioimaging Applications," ACS Applied Materials & Interfaces, 2020, vol. 12, pp. 31217-31224.

Xue, D-X. et al., "Tunable Rare Earth fcu-MOF Platform: Access to Adsorption Kinetics Driven Gas/Vapor Separations via Pore Size Contraction," Journal of the American Chemical Society, 2015, vol. 137, pp. 5034-5040.

\* cited by examiner

TARGETED NEAR-INFRARED IMAGING BY METAL-ORGANIC FRAMEWORKS

CROSS-REFERENCE TO RELATED APPLICATIONS

This application is a continuation-in-part of application Ser. No. 15/994,904, filed May 31, 2018, which claims the benefit of U.S. Provisional Application No. 62/522,006, filed Jun. 19, 2017, both of which are incorporated herein by reference.

STATEMENT OF GOVERNMENT INTEREST

This invention was made with Government support under Contract No. DE-NA0003525 awarded by the United States Department of Energy/National Nuclear Security Administration. The Government has certain rights in the invention.

FIELD OF THE INVENTION

The present invention relates to biomedical imaging and, in particular, to targeted near-infrared imaging of biological materials by metal-organic frameworks.

BACKGROUND OF THE INVENTION

The rational design of made-to-order novel materials systems with low toxicity, ease of synthesis, and which can perform multiple/complex tasks for biologically relevant applications (cargo delivery and/or bio-imaging) has become of great interest in recent years. One area of growing concentration is the application of metal-organic frameworks (MOFs) to the field of therapeutic delivery and biomedical imaging. MOFs for biomedical imaging have been developed for magnetic resonance imaging (MRI), computed tomography (CT), Positron Emission Tomography (PET), intracellular biosensing and optical imaging. See J. Della Rocca et al., *Acc. Chem. Res.* 44, 957 (2011); K. Lu et al., *Adv. Mater.* 30, 1707634 (2018); H. Wang, *Coor. Chem. Rev.* 349, 139 (2017); and S. E. Miller et al., *Interface Focus* 6, 20160027 (2016).

In the arena of optical imaging for biomedicine, there are two main areas of focus, visible and near-infrared (NIR) imaging. NIR imaging in the first window (NIR-I, 700-900 nm) has been successful in clinical use but is limited by poor tissue penetration and a high degree of light scattering, leading to limited spatial resolution and restricted imaging uses. Recently, improvements in camera technologies have opened the potential of second NIR window imaging (NIR-II, 1000-1300 nm) which has reduced photon absorption from tissue components and reduced scattering effects. See Z. Starosolski et al., *PLoS ONE* 12, e0187563 (2017). MOFs have been designed for imaging within the NIR windows utilizing Yb or incorporation of the NIR dye, indocyanine green. See K. Lu et al., *Adv. Mater.* 30, 1707634 (2018); W. Cai et al., *ACS Appl. Mater. Interfaces* 9, 2040 (2017); and A. Foucault-Collet et al., *Proc. Natl. Acad. Sci.* 110, 17199 (2013).

While NIR imaging has a history of clinical application, the spatial resolution is still limited and optical imaging in the visible spectrum is utilized to understand the microscopic interactions of MOFs and other nanomaterials with cells. See K. M. L. Taylor-Pashow et al., *J. Am. Chem. Soc.* 131, 14261 (2009); D. Liu et al., *Angew. Chem. Int. Ed.* 50, 3696 (2011); and R. Nishiyabu et al., *J. Am. Chem. Soc.* 131, 2151 (2009). MOF-based photoluminescence can be achieved through incorporation of fluorescent linkers, encapsulation of fluorescent dyes or via intrinsic emission properties of the metals. See S. E. Miller et al., *Interface Focus* 6, 20160027 (2016). MOF luminescent imaging can also be done in vivo in rodent models, allowing tracking of biodistribution of MOF nanocarriers. See R. Nishiyabu et al., *J. Am. Chem. Soc.* 131, 2151 (2009); and X. Gao et al., *Dalton Trans.* 46, 13686 (2017). Additionally, many in vivo imaging modalities, such as MRI, lack detailed spatial resolution necessary to determine the specific cellular interaction in tissues. As the specific cellular interaction, such as cell type, can be highly important for diagnostic imaging and therapeutic delivery, mixed metal MOFs with a visible optical signal as well as MRI signature have been created. See X. Gao et al., *Dalton Trans.* 46, 13686 (2017); W. J. Rieter et al., *J. Am. Chem. Soc.* 128, 9024 (2006); and G. D. Wang et al., *Tomography* 2, 179 (2016).

SUMMARY OF THE INVENTION

The present invention is directed to a near-infrared imaging metal-organic framework, comprising a plurality of metal clusters, each cluster comprising one or more rare earth metal ions, and a plurality of carboxylic acid-based linkers coordinating with the plurality of metal clusters, wherein the carboxylic acid-based linkers further comprise one or more amine groups within the linker. The rare earth metal can comprise Nd, Yb, Eu, Y, Ce, Pr, Sm, Gd, Tb, Dy, Ho, Er, Tm, or mixtures thereof. The at least one metal cluster can comprise a first rare earth metal ion and a second rare earth metal ion that is different from the first rare earth metal ion. The carboxylic acid-based linker can comprise an amino-containing di-, tri-, tetra-, or hexacarboxylic acid. A large variety of biologically relevant molecules can be conjugated to the MOF including, but not limited to, peptides, proteins (e.g., avidin, CD47, fibrinogen, bovine serum albumin, clusterin, hydrophobin, T-cell receptors, antibodies, and enzymes), nucleic acids (e.g., ribonucleic acids, deoxyribonucleic acids, and peptide nucleic acids), nanobodies, and polymers that can alter biological behavior (e.g., polyethylene glycol, chitosan, and poly(D,L-lactic-co-glycolic acid)).

The present invention further comprises a method for targeted near-infrared imaging, comprising providing a metal-organic framework and conjugating a biological molecule to the metal-organic framework via an amine group within the linker. The amino functional group enables biological based conjugation in a MOF with predetermined features. As an example of the invention, antibodies were conjugated to the available amino group utilizing a common conjugation method, carbodiimide chemistry, and a more specialized chemistry utilizing sulfhydryl chemistry via Traut's reagent. This latter method of chemical conjugation has significant advantages in the realm of biological conjugations due to the ability to utilize cysteine residues within proteins or add these residues to the end of the protein. Further, the ability of an epithelial cell adhesion molecule (EpCAM) antibody targeted MOFs to bind to their target cells and be imaged via confocal microscopy was demonstrated. In addition to binding a single antibody to the MOF, the targeting capability can be expanded to additional targeting moieties. Other biologically relevant proteins can also be targeted to further alter the MOF interaction with cells. This family of RE-containing MOFs with amino functional groups can provide combined visible/NIR emitting MOFs to expand the targeting capabilities into the visible and NIR-I and NIR-II imaging windows.

BRIEF DESCRIPTION OF THE DRAWINGS

The detailed description will refer to the following drawings, wherein like elements are referred to by like numbers.

FIG. 10A is a graph showing NanoOrange protein quantitation to confirm the conjugation of the NeutrAvidin protein and the EpCAM antibody to the Eu-2-amino-BDC particles. FIG. 10B is a graph showing fluorescently labeled secondary antibody to the EpCAM antibody to confirm the conjugation of EpCAM antibody to the NeutrAvidin conjugated Eu-2-amino-BDC particles.

DETAILED DESCRIPTION OF THE INVENTION

Figure 1B:
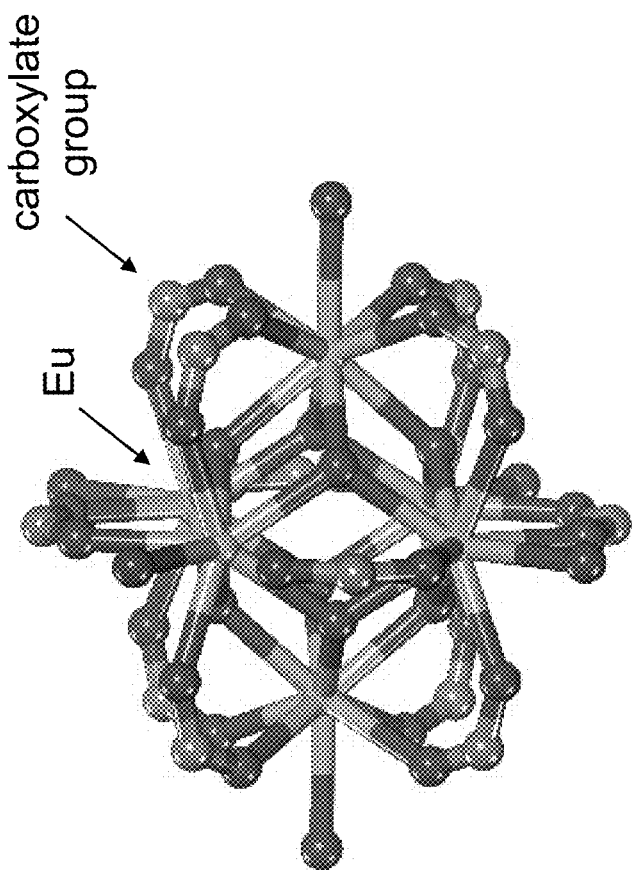
FIG. 1B illustrates a representative targeted Eu hexanuclear cluster.

MOFs incorporate single metal ions or clusters of metal ions connected by organic linkers that can efficiently sensitize luminescent metal ions. A multifunctional biocompatible MOF materials platform based on rare earth metal ions has been recently reported. See D. F. Sava Gallis et al., *ACS Appl. Mater. Interfaces* 9, 22268 (2017). These MOF materials are amenable for bioimaging applications, in the visible range and in both NIR windows. Subsequent studies have focused on tuning of particle size with emphasis on increasing quantum yield in these materials systems. These materials have produced the highest quantum yield observed in NIR-emitting MOFs to date. See D. F. Sava Gallis et al., *CrystEngComm* 20, 5919 (2018).

Primary amine groups represent one of the most versatile chemical moieties for conjugation to biologically relevant molecules, such as fluorescent labels, nucleic acids, peptides and proteins (including antibodies and enzymes), which can have limited or no stability in non-aqueous, low pH, high pH, or high temperature reaction environments. See R. Kazlauskas, R., *Chem. Soc. Rev.* 47, 9026 (2018); and Y. Le Basle et al., *J. Pharm. Sci.* 109, 169 (2020). In biologically relevant chemical reactions, primary amines can form chemical bonds with a wide variety of synthetic chemical groups including isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl esters. See G. T. Hermanson, Chapter 2—Functional Targets for Bioconjugation, in Bioconjugate Techniques (Third Edition), Hermanson, G. T., Ed. 2013; pp 127-228.

The present invention is directed to a targeted imaging agent, as facilitated by both the facile chemistry of the MOFs, in general, and the highly tunable nature of this materials platform, in particular. For example, the ability to chemically bind antibodies to MOFs is highly relevant for use in a wide variety of assays and as novel targeted imaging agents for biological/medical imaging. See S. Wang et al., *Adv. Mater.* 30, 1800202 (2018).

The present invention is further directed to MOFs that comprise rare earth metals that form metal clusters that are coordinated with carboxylic acid-based linkers, wherein the carboxylic acid-based linkers comprise one or more amine groups. Examples of rare earth metals that can be used include Nd, Yb, Eu, Y, Ce, Pr, Sm, Gd, Tb, Dy, Ho, Er, and Tm. These rare earth metals will result in distinct emission properties. A variety of carboxylic acid-based linkers can be used to connect the metal clusters, including amino analogs of di-, tri-, tetra-, and hexacarboxylic acids. Exemplary linear dicarboxylic acid linkers include 4,4'-stilbenedicarboxylic acid, 2,2'-dinitro-4,4'-stilbenedicarboxylic acid, 2'2-diamino-4,4'-stilbenedicarboxylic acid, 2,5-dihydroxyterephthalic acid (DOBDC), 4,4'-biphenyl dicarboxylic acid, and 1,4-napthalene dicarboxylic acid. Exemplary tricarboxylic acid linkers include 1,3,5-tris(4-carboxyphenyl)benzene (BTB), 4,4',4"-5-triazine-2,4,6-triyl-tribenzoic acid (TATB), and 1,3,5-tris(4'-carboxy[1,1'-biphenyl]-4-yl)benzene (TCBB). Exemplary tetracarboxylic acid linkers include 1,2,4,5-tetrakis(4-carboxyphenyl)benzene (TCPB) and 1,3, 6,8-tetra(4/carboxyphenyl)pyrene (TBAP). An exemplary hexacarboxylic acid linker includes 1,2,3,4,5,6-hexakis(4'-carboxylato(1,1'-biphenyl)-4-yl)benzene. A linear linker, such as DOBDC, will likely form hexanuclear metal clusters. Tetratopic linkers, such as TCPB, will likely form nonanuclear metal clusters. See U.S. application Ser. No. 15/994,904, filed May 31, 2018, which is incorporated herein by reference.

The invention is further directed to rare-earth MOFs (RE-MOFs) comprising analogs of carboxylic acid-based linkers that further comprise one or more primary amines within the linker that are available for conjugation to biologically relevant molecules. As an example of the invention, 2-aminoterephthalic acid (2-amino-BDC) was used to synthesize the Eu-based analog of the originally reported EuDOBDC material based on a 2,5-dihydroxyterephthalic acid (DOBDC) linker. See D. F. Sava Gallis et al., *ACS Appl.*

Figure 1A:
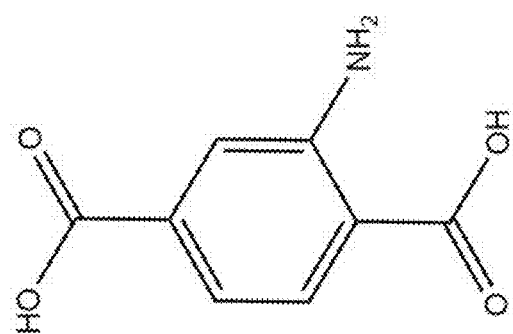
FIG. 1A shows the 2-aminoterephthalic acid linker molecule.

*Mater. Interfaces* 9, 22268 (2017). The exemplary 2-aminoterephthalic acid molecule is shown in FIG. 1A. A predetermined/targeted hexanuclear metal cluster of the exemplary Eu-2-amino-BDC MOF is depicted in FIG. 1B, showing carboxylate groups of the 2-amino-BDC linker molecules bridging the Eu atoms of the metal cluster.

The availability and chemical utility of the primary amine within the organic linker for cell targeting is described below. Amine specific reactions were demonstrated through two different chemical conjugations schemes based on: (i) carbodiimide chemistry to link the primary amine to available carboxyl groups on the protein NeutrAvidin; and (ii) primary amine reaction to add a reactive sulfhydryl group, via the Traut's reagent, to specifically react maleimide-activated NeutrAvidin and to demonstrate sulfhydryl cross-linking chemistry on the MOF. As will be described below, detailed materials characterization was used to probe the phase purity, particle size, photoluminescence properties and functionality of the targeted Eu-2-amino-BDC material.

Eu-2-Amino-BDC Synthesis and Characterization

Figure 2:
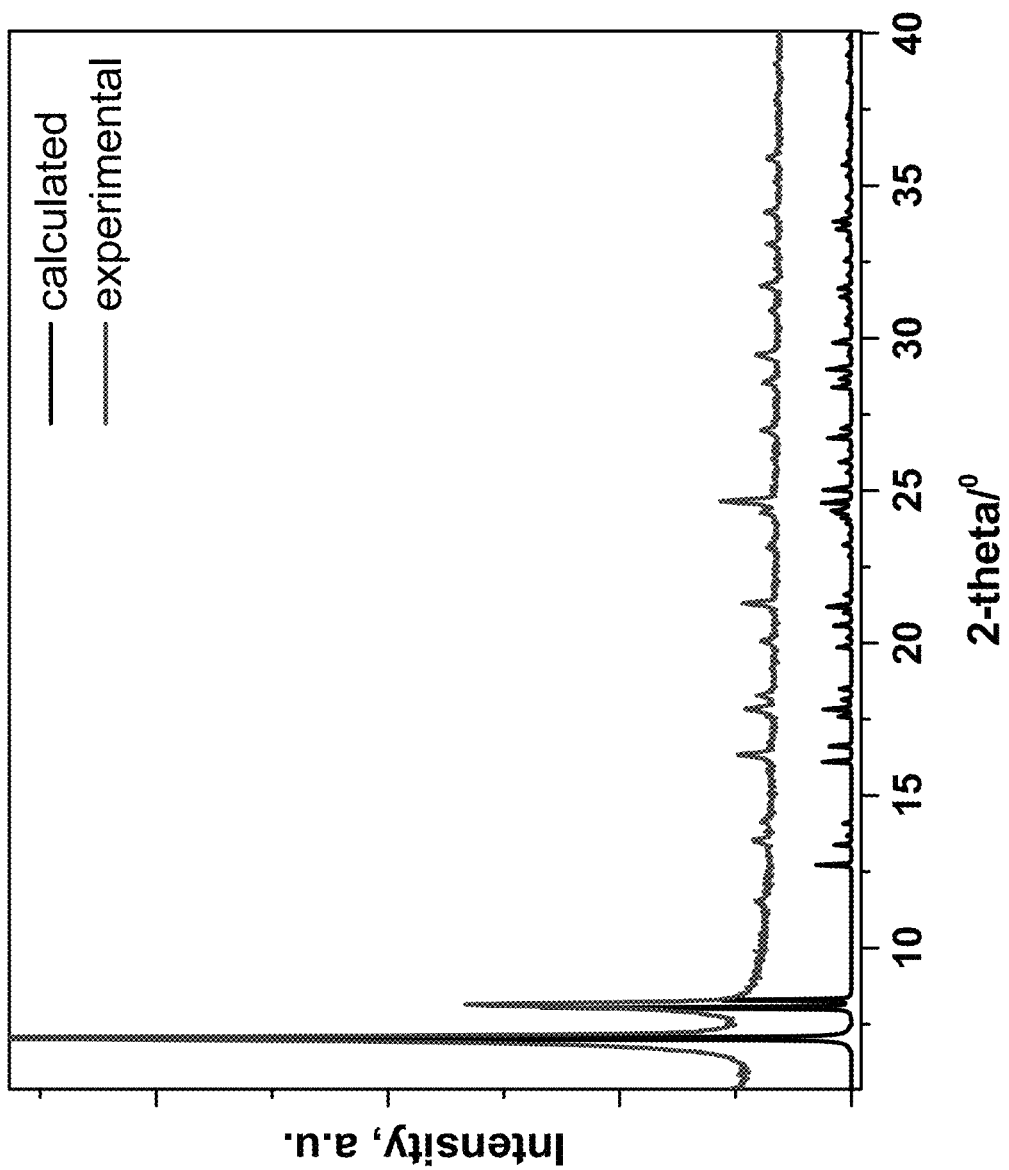
FIG. 2 is a graph of powder X-ray diffraction (XRD) patterns of calculated EuDOBDC as compared to that experimentally measured on an Eu-2-amino-BDC sample.

The synthesis of the Eu-2-amino-BDC material was performed using a microwave-assisted approach. A reaction mixture containing $EuCl_3.6H_2O$ (0.0172 g, 0.047 mmol), 2-aminoterephthalic acid (0.0124 g, 0.068 mmol), 2-fluorobenzoic acid (2-FBA, 0.205 g, 1.463 mmol), and N,N'-dimethylformamide (DMF, 2 mL) was placed in a 10 mL microwave vial with a stir bar and was heated to 175° C. for 40 minutes with a 15s pre-mix. The reaction was then washed 3× in DMF followed by 3× in ethanol. FIG. 2 shows the very good correlation between the calculated EuDOBDC powder X-ray diffraction pattern and that measured experimentally on the crystalline Eu-2-amino-BDC material. This indicates that the two materials are structurally analogous and that the newly synthesized phase is pure.

As one of the most common needs for biological imaging is specific targeting utilizing biological targeting agents such as antibodies, and because antibodies typically require aqueous environments with the presence of salts, the suitability of the Eu-2-amino-BDC material for chemical conjugations for biologically relevant applications was investigated. Since MOFs have been found to have reduced stability in full strength phosphate-buffered saline (PBS), a common biologically relevant buffer used for conjugations, the full strength PBS was diluted with water. See D. Liu et al., *Angew. Chem. Int. Ed.* 50, 3696 (2011); G. D. Wang et al., *Tomography* 2, 179 (2016); and D. F. Sava Gallis et al., *ACS Appl. Mater. Interfaces* 11, 7782 (2019). The Eu-2-amino-BDC particle stability in water and a PBS/water mixture was evaluated for 6 hrs and 1 day. The times were selected to test conditions likely for common conjugation reactions and conjugation plus short-term storage before use. Powder X-ray diffraction patterns showed no change to crystalline structure of the Eu-2-amino-BDC material under the tested conditions.

Figure 3B:
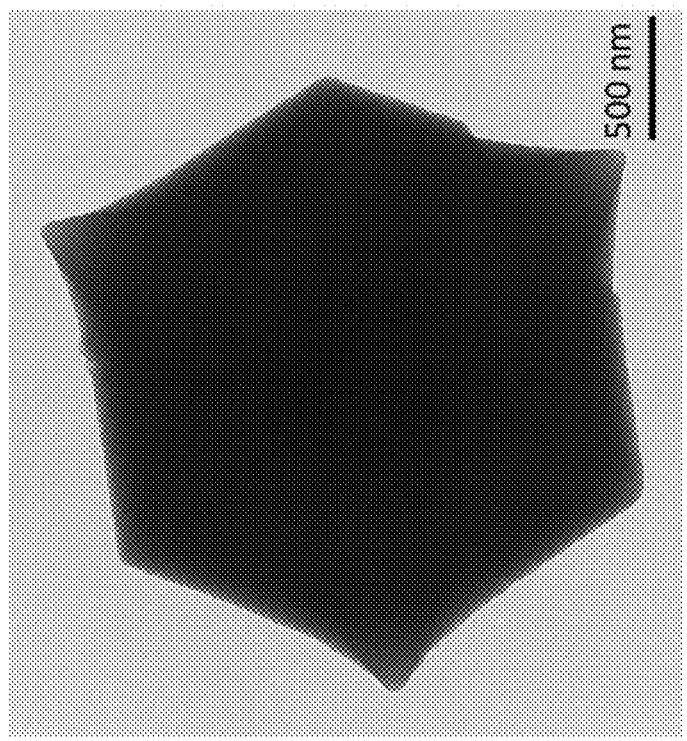
FIG. 3B is a representative transmission electron microscope (TEM) image for the Eu-2-amino-BDC material.
Figure 3A:
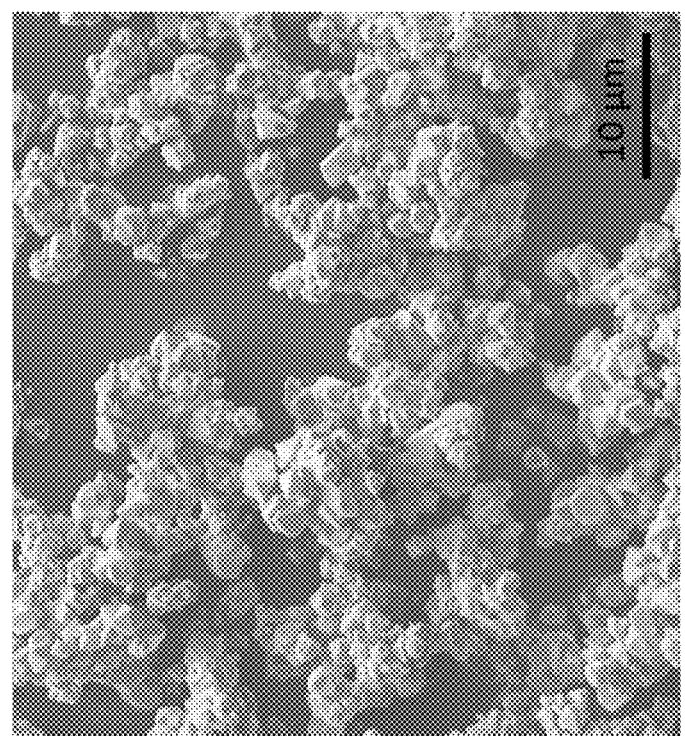
FIG. 3A is a representative scanning electron microscope (SEM) image for the Eu-2-amino-BDC material.

Additional insights into the particle size and morphology were provided by electron microscopy. FIG. 3A reveals the relative uniform particles size in the Eu-2-amino-BDC material, as characterized by SEM microscopy. Further, the TEM image in FIG. 3B shows the representative polyhedral morphology of an individual particle.

Figure 4:
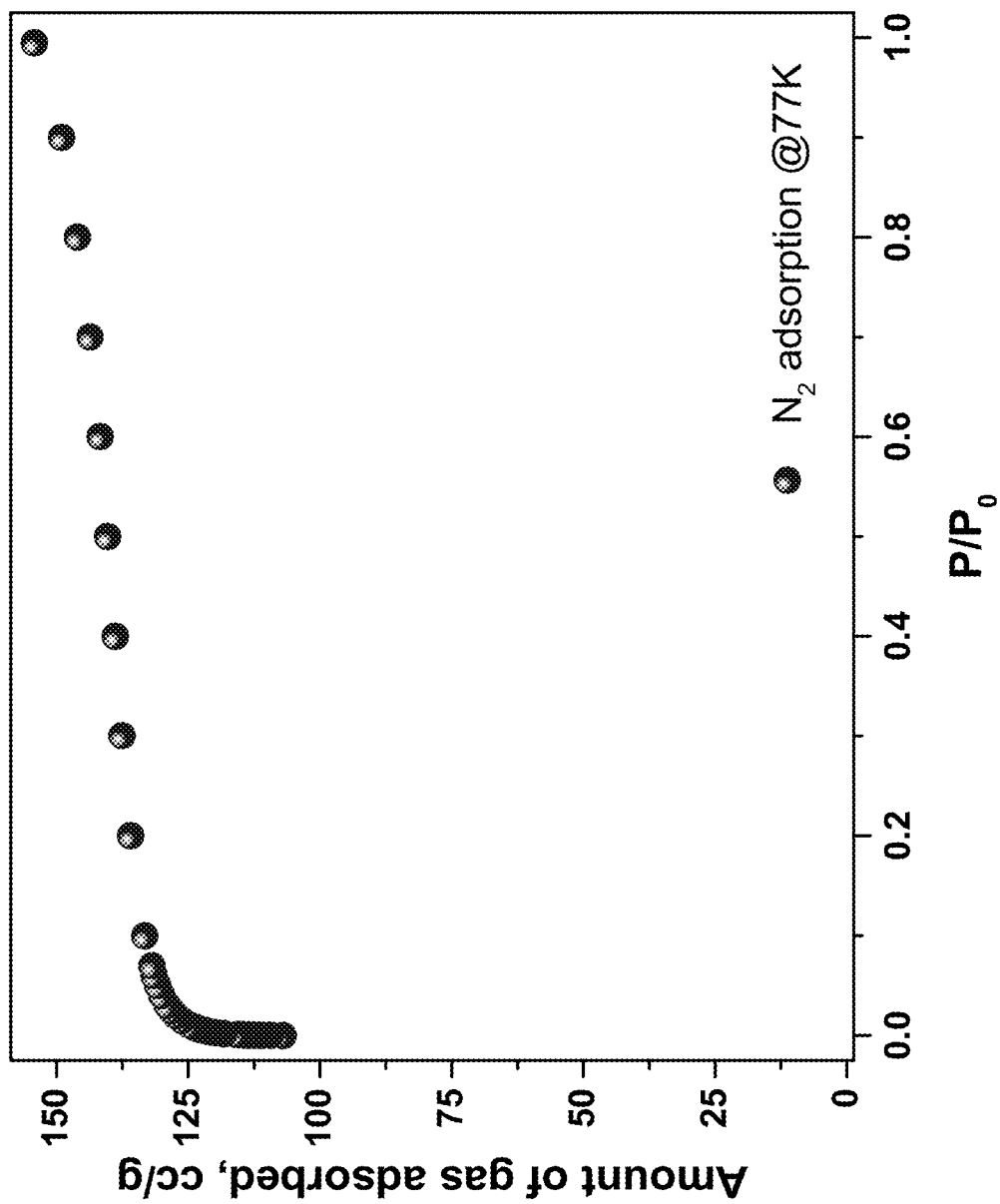
FIG. 4 is a graph of nitrogen adsorption isotherm measured at 77K on the Eu-2-amino-BDC sample.

Finally, the material structural characterization was completed with the nitrogen adsorption isotherm measured at 77K, as shown in FIG. 4, employed here to confirm microporosity in this newly synthesized material. The BET surface area was calculated to be 548 $m^2/g$. This is comparable with that of the previously reported micron-sized particles for the EuDOBDC analog (700 $m^2/g$) and considerably higher than the surface area of EuDOBDC nanoparticles (315 $m^2/g$). See D. F. Sava Gallis et al., *ACS Appl. Mater. Interfaces* 9, 22268 (2017). Reduced porosity in nanosized MOFs has been previously observed in other systems, and it is likely related with only partial pore guests removal. See J. Cravillon et al., *Chem. Mater.* 21, 1410 (2009). This is supported by the fluorine content associated with the fluorobenzoic acid modulator used in this synthesis, as identified via SEM-EDS analyses.

Photoluminescent Properties

Figure 5:
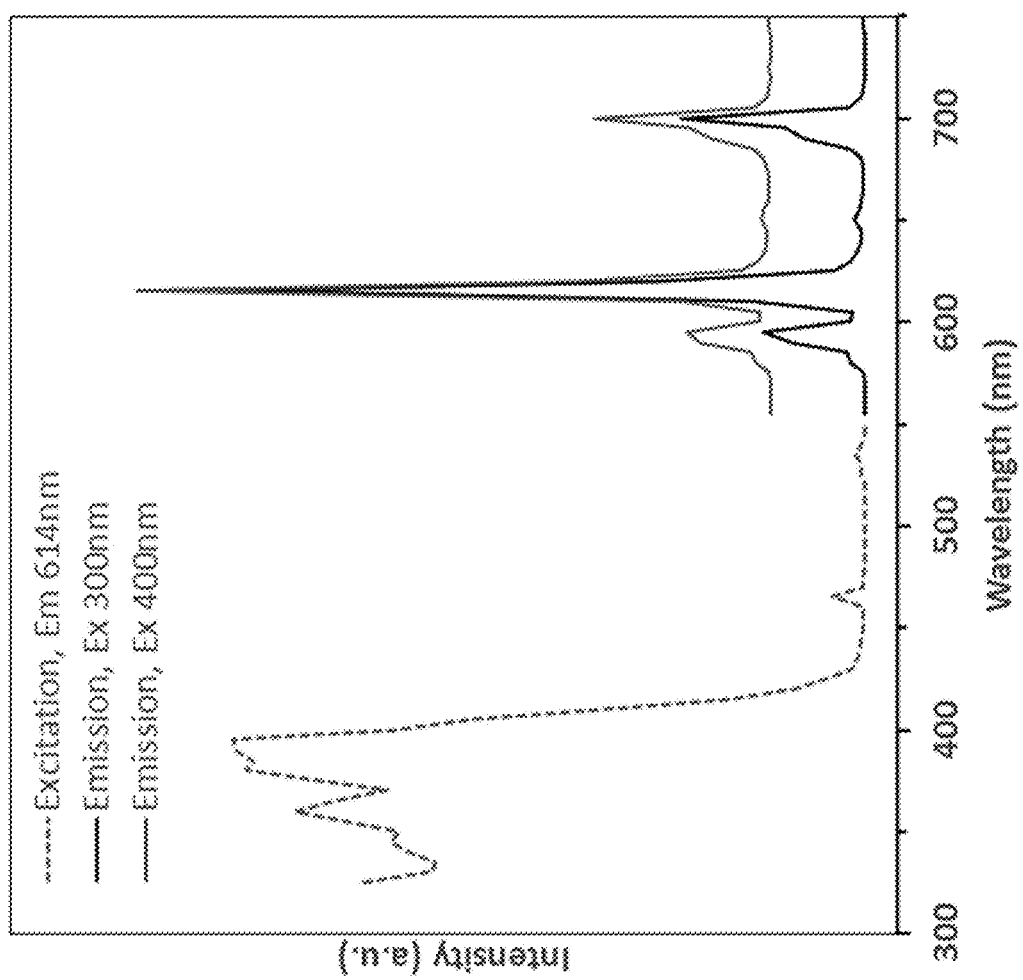
FIG. 5 is a graph of photoluminescence excitation (PLE) and emission (PL) spectra for the Eu-2-amino-BDC sample; the emission spectra are offset for clarity.

The photoluminescent properties of the Eu-2-amino-BDC MOF were examined to confirm utility for biological imaging, as shown in FIG. 5. Prior research has demonstrated that the originally reported EuDOBDC material displays broad excitation below 425 nm. The Eu-2-amino-BDC sample also showed the anticipated broad excitation below 425 nm, which is applicable to most laser microscopy systems for biological imaging which utilize Ar-UV lasers emitting at 351 nm and 364 nm, or 405 nm diode lasers. To examine the variability of emission within the commonly expected excitation ranges for microscopy, emission spectra were taken with excitation at 300 nm and 400 nm. The Eu-2-amino-BDC MOF also retained the narrowband emission peaks between 590 and 725 nm found previously with EuDOBDC and other Eu-containing MOFs. See X. Gao et al., *Dalton Trans.* 46, 13686 (2017); W. J. Rieter et al., *J. Am. Chem. Soc.* 128, 9024 (2006); and D. F. Sava Gallis et al., *ACS Appl. Mater. Interfaces* 9, 22268 (2017). Additionally, the emission spectra showed no change between excitation at 300 nm or 400 nm, similar to the observed lack of change in emission spectra of the EuDOBDC MOF with changing excitation.

To determine if the spectral properties of the Eu-2-amino-BDC particles could be detected via microscopy, the spectral properties were assessed utilizing spectral scanning on a confocal microscope. The Eu-2-amino-BDC particles, when deposited in cell mounting media and excited by a 405 nm laser, retained their spectral characteristics, showing narrow bands of emission between 575 and 710 nm. Additionally, a broad peak from 425 to 575 nm was observed which was attributed to the linker emission. As laser power can be varied on a confocal microscope and higher laser power can be damaging to cells, the required laser power to visualize the Eu-2-amino-BDC particles was assessed. The spectral characteristics were readily visible with 5% laser power, even with the narrow collection band used for spectral scanning of 5 nm. 5% laser power is within the acceptable range for cell imaging, demonstrating the potential utility of the Eu 2-amino-BDC particles for bioimaging.

Biocompatibility, Antibody Targeting and Bioimaging

After confirmation of the anticipated luminescent properties, the Eu-2-amino-BDC particles were assessed for biocompatibility as measured by alterations in cell viability to mammalian cells. A human epithelial cell line (A549) and a mouse macrophage cell line (RAW 264.7) were chosen as epithelial cells are common targets for imaging studies and macrophages are involved in the clearance of injected particle materials. See G. Song et al., *Curr. Rheumatol. Rev.* 10, 22 (2014); and S. Park et al., *Nat. Rev. Mater.* 2, 17104 (2017).

To assess cell viability, A549 were maintained in F-12K+ 10% fetal bovine serum (FBS, by volume) and RAW 264.7 cells were maintained in DMEM+4 mM L-glutamine+10% FBS (by volume). For cell viability assessment, 5,000 cells were plated per well in 100 µL media in 96 well plates and allowed to adhere overnight. Fresh media containing Eu-2-amino-BDC at varied concentration (0-500 µg/mL) were then prepared. Cell exposure was performed by removing media from the adherent cells, and then replacing it with freshly prepared media containing Eu-2-amino-BDC. Cells were incubated with Eu-2-amino-BDC MOF for 24 or 48 hours at standard cell culture conditions (37° C. and 5% $CO_2$). After exposure, cell viability was assessed using CellTiter-Glo 2.0 Assay (Promega) utilizing the standard protocol with luminescence measured by a BioTek Synergy Neo2 microplate reader. The cell viability was calculated as a percentage of mock treated sample. Cell viability measurements were done in quadruplicate and graphed as the average and standard deviation.

Figures 6A, 6B:
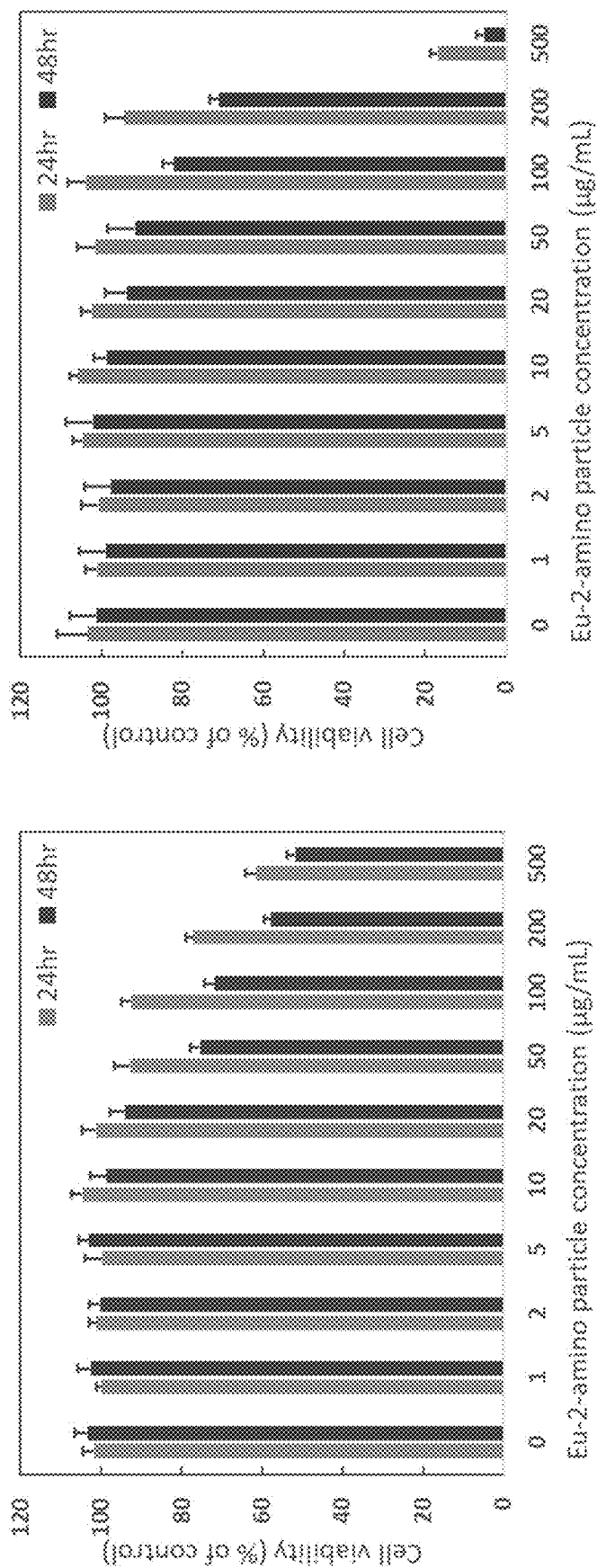
FIG. 6A is a graph of cell viability of the A549 human lung epithelial cell line after 24 and 48 h exposure to Eu-2-amino particles.
FIG. 6B is a graph of cell viability for the RAW 264.7 mouse macrophage cell line after 24 and 48 h exposure to Eu-2-amino particles.

As shown in FIGS. 6A and 6B, both epithelial and macrophage cell viability was assessed after 24 and 48 h exposures at sample concentrations ranging from 1-500 µg/mL. With both epithelial and macrophage cell lines, there is a dose dependent increase in toxicity. In both cell lines, the cell viability was greater than 75% at 200 µg/mL at 24 hours. The high cell viability at 24 h was previously seen with other RE-containing MOFs including Eu-containing MOFs. See D. F. Sava Gallis et al., *ACS Appl. Mater. Interfaces* 9, 22268 (2017). However, at high doses, an increase in toxicity is visible with longer exposure with the survival at 200 µg/mL dropping from 77% to 58% in epithelial cells and 94% to 71% in macrophage cells as exposure time increased from 24 to 48 h. Even at 48 h the toxicity of the Eu-2-amino-BDC particles is low, with greater than 75% cell viability at 50 µg/mL in the epithelial line and 100 µg/mL in the macrophage line. This low level of cytotoxicity is consistent with other reports with microscale MOFs. See D. F. Sava Gallis et al., *CrystEngComm* 20, 5919 (2018); D. F. Sava Gallis et al., *ACS Appl. Mater. Interfaces* 9, 22268 (2017); and Q. Hu et al., *J. Med. Chem.* 57, 5679 (2014). There is also a difference in toxicity effect between the cell lines, as the epithelial cell line shows more significant toxicity at most doses and the macrophage line showing high toxicity at the 500 µg/mL dose compared to the epithelial cells. Variability in response by cell type is one of the reasons for studying multiple cell types and has been previous observed with a variety of MOFs. See D. F. Sava Gallis et al., *CrystEngComm* 20, 5919 (2018); D. F. Sava Gallis et al., *ACS Appl. Mater. Interfaces* 9, 22268 (2017); D. F. Sava Gallis et al., *ACS Appl. Mater. Interfaces* 11, 7782 (2019); and C. Tamames-Tabar et al., *J. Mater. Chem. B* 2, 262 (2014).

Next, the ability of the linker amino group within the Eu-2-amino-BDC particles to be utilized for protein conjugation was assessed. A number of conjugation methodologies, both covalent and coordinative, have been explored for surface functionalization of MOFs. See S. Wang et al., *Adv. Mater.* 30, 1800202 (2018). One of the more common methodologies is utilizing carbodiimide chemistries to link proteins, such as streptavidin, tryspin or antibodies, to various MOFs. See P. Ling et al., *Anal. Chem.* 87, 3957 (2015); X. Qi et al., *Chem. Mater.* 29, 8052 (2017); Y. Shih et al., *ChemPlusChem* 77, 982 (2012); and C. van der Wel et al., *Langmuir* 33, 9803 (2017).

Figure 7:
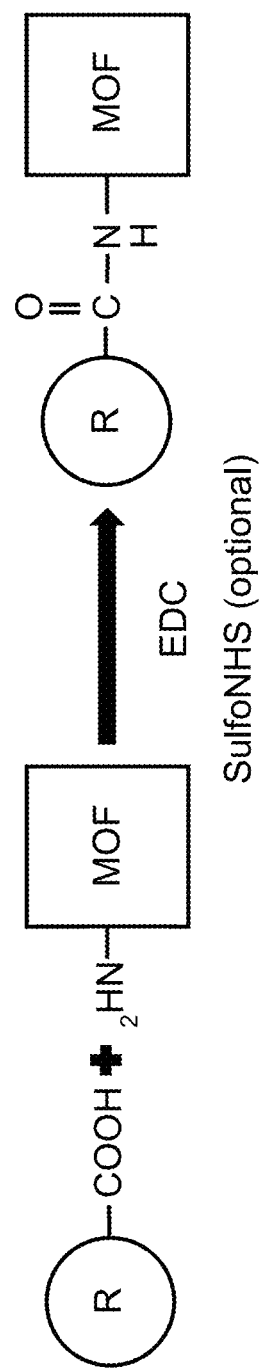
FIG. 7 illustrates a method to conjugate a primary amine group on a MOF linker with a carboxylic acid group on a biological molecule using carbodiimide chemistry.

Carbodiimide chemistry links a primary amine group on the MOF linker with a carboxylic acid on a biological molecule (R) to form a carboxamide bond, as shown in FIG. 7. Although multiple versions of this conjugation method can be used, water-soluble versions of this chemistry using 1-ethyl-3-(3-dimethylaminopropyl) carbodiimide hydrochloride (EDC) and N-hydroxysulfosuccinimide (Sulfo-NHS) are the most common. Sulfo-NHS is not required, but it does increase the reaction efficiency. Importantly, no part of these chemicals is incorporated into the resulting carboxamide bond between the biological molecule and the MOF. Alternatively, carboxylic acid moieties on the MOF can link to primary amines within the biological molecule. An advantage of this chemistry is that carboxylic acids are very common in biology. Note that multiple biological molecules can be attached to a single MOF using this chemistry. A potential disadvantage is that, because of the ubiquity of such groups, it can be difficult to control the orientation of the conjugated molecule or protein.

To confirm that the inclusion of the amine moiety within the particle did not alter the ability to utilize this common chemistry, EDC and Sulfo-NHS were used to conjugate the streptavidin variant, NeutrAvidin, to the surface of the Eu-2-amino-BDC particles. As carbodiimide chemistry (i) can utilize any primary amine and any carboxylic acid to create a linkage and (ii) proteins have many primary amines and carboxylic acids, the chemical conjugation can link proteins together which can create large agglomerations of proteins and particles. To prevent this possibility, a 2-step procedure was utilized, where the EDC and Sulfo-NHS were used to activate the amine within the Eu-2-amino-BDC in the absence of the NeutrAvidin protein. The activated Eu-2-amino-BDC particles were then conjugated with the NeutrAvidin.

As a specific example, to conjugate antibodies to Eu-2-amino-BDC via carbodiimide chemistry, 120 µg of Eu-2-amino-BDC was collected via centrifugation (5,000 RCF for 10 min) and resuspended in sterile filtered $H_2O$ at 1 mg/mL. To the Eu-2-amino-BDC MOFs in water, 170 µL of freshly prepared solution of 400 mM 1-ethyl-3-(3-dimethylaminopropyl) carbodiimide hydrochloride (EDC) and 100 mM N-hydroxysulfosuccinimide (Sulfo-NHS) in $H_2O$ was added. The reaction was allowed to proceed for 20 minutes at room temperature with mixing to activate the amines with NHS ester groups. The activated Eu-2-amino-BDC particles were then collected via centrifugation (10,000 RCF for 10 min) and resuspended in sterile filtered $H_2O$. The centrifugation step was then repeated, and the activated particles were resuspended in 200 µL of sterile filtered $H_2O$ containing 0.12 mg of NeutrAvidin. Reaction was allowed to proceed for 2.5 h at room temperature with mixing to conjugate NeutrAvidin to the activated MOF surface. The avidin-conjugated Eu-2-amino-BDC particles were then collected via centrifugation (10,000 RCF for 10 min) and resuspended in PBS diluted 1:6 with sterile filtered $H_2O$. After dilution with water, the concentration of salts was NaCl 25.86 mM, $Na_2HPO_4$ 0.49 mM and $KH2PO_4$ 0.18 mM in the 1:6 PBS solution. The centrifugation step was then repeated, and the particles were resuspended in 120 µL PBS diluted 1:6 with sterile filtered $H_2O$. To the avidin-conjugated Eu-2-amino-BDC particles, 10 µg of biotinylated mouse anti-human EpCAM antibody (Invitrogen, clone 187) was added. The particles were incubated with the antibody for 60 min at room temperature to bind the antibodies to the avidin-conjugated particles. The antibody-conjugated Eu-2-amino-BDC particles were then collected via centrifugation (10,000 RCF for 10 min) and resuspended in PBS diluted 1:6 with sterile filtered $H_2O$. The centrifugation step was then repeated, and the antibody-conjugated particles were resuspended in PBS diluted 1:6 with sterile filtered $H_2O$ at 1 mg/mL and stored at 4° C. until use.

Figure 8:
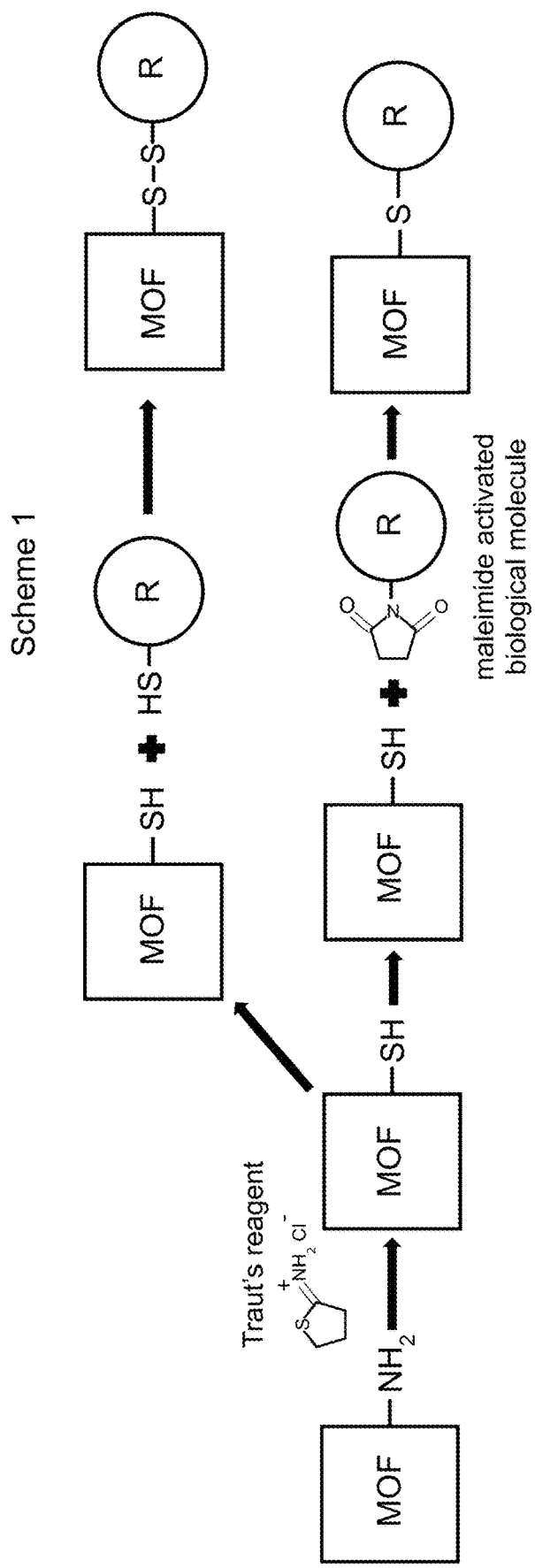
FIG. 8 illustrates a method to conjugate a MOF to a biological molecule using thiolation chemistry.

Carbodiimide chemistry can also affect protein and antibody function through blocking or alteration of necessary sites on the protein. By switching the carboxylic acid within the MOF linker to an amine, additional chemical opportunities become available, such as thiolation of the MOF with Traut's reagent to convert the amino group to a sulfhydryl group, as shown in FIG. 8. Sulfhydryl groups can react with each other to form disulfide bonds, as shown in Scheme 1. This approach enables direct conjugation to a wide variety of peptides and proteins, including antibodies and enzymes. Thiol-modified DNA can also be attached using this method. An advantage of this method is that thiol group reactions allow more specificity in attaching the biological molecule to the MOF. For example, because sulfhydryl groups are relatively rare in proteins, the sulfhydryl group can be specifically added to proteins at controlled locations, making the conjugation sites much more specific than carbodiimide chemistry. In addition to self-reaction with other sulfhydryl groups, the sulfhydryl group of the thiolated MOF can be reacted with a maleimide group on the biological molecule to create a stable thioether bond, as shown in Scheme 2.

Figure 9:
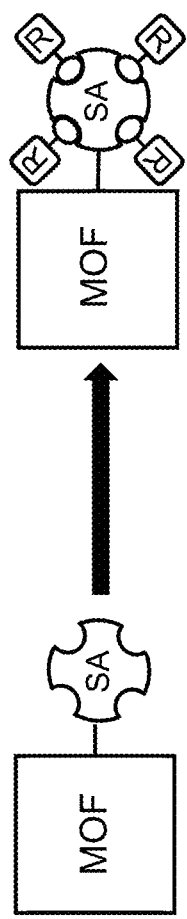
FIG. 9 illustrates a method to bind biotinylated molecules to a streptavidin molecule attached to a MOF.

An advantage of attaching streptavidin and variants to the MOF is that these homo-tetramers have a very high affinity for biotin and will react with any biotinylated substrate. Further, it is easy to get a wide variety of biological molecules biotinylated, including peptides, proteins (including antibodies and enzymes), nucleic acids (including PNA and DNA), and polymers. Once attached to the MOF, streptavidin (SA) can bind up to 4 biotinylated molecules (R), as shown in FIG. 9. As an example, the Traut's based chemistry was used to link maleimide-activated NeutrAvidin to the thiolated Eu-2-amino-BDC particles. This type of chemistry has previously been applied to other particles, but has not been applied for protein conjugation to MOFs. See P. N. Durfee et al., *ACS Nano* 10, 8325 (2016); and M. R. Villegas et al., *Chem. Mater.* 30,112 (2018). Following NeutrAvidin conjugation, the NeutrAvidin was used to attach a biotinylated antibody to epithelial cellular adhesion molecule (EpCAM) to the Eu-2-amino-BCD particles.

As a specific example, to conjugate antibodies to Eu-2-amino-BDC via thiolation chemistry, 120 μg of Eu-2-amino-BDC was collected via centrifugation (5,000 RCF for 10 min) and resuspended in sterile filtered $H_2O$ at 1 mg/mL. To the Eu-2-amino-BDC MOFs in water, 50 μL of freshly prepared 250 mM Traut's reagent (2-iminothiolane) in $H_2O$ was added to convert the surface NH2 groups to SH groups. The reaction was allowed to proceed at room temperature with mixing for 1 h. The thiolated Eu-2-amino-BDC particles were then collected via centrifugation (10,000 RCF for 10 min) and resuspended in $H_2O$. The centrifugation step was then repeated, and the thiolated particles were resuspended in 120 μL of sterile filtered $H_2O$. The resuspended Eu-2-amino-BDC particles were added to an Eppendorf tube containing 0.10 mg of maleimide-activated NeutrAvidin. The reaction was allowed to proceed for 2.5 h at room temperature with mixing to conjugate the maleimide-activate NeutrAvidin to the thiolated particles. The avidin-conjugated Eu-2-amino-BDC particles were then collected via centrifugation (10,000 RCF for 10 min) and resuspended in PBS diluted 1:6 with sterile filtered $H_2O$. Centrifugation step was then repeated, and the particles were resuspended in 120 μL PBS diluted 1:6 with sterile filtered $H_2O$. To the avidin-conjugated Eu-2-amino-BDC particles, 10 μg of biotinylated mouse anti-human EpCAM antibody (Invitrogen, clone 187) was added. The particles were incubated with the target antibody for 60 min at room temperature to bind the antibodies to the avidin-conjugated particles. The antibody-conjugated Eu-2-amino-BDC particles were then collected via centrifugation (10,000 RCF for 10 min) and resuspended in PBS diluted 1:6 with sterile filtered $H_2O$. The centrifugation step was then repeated, and the antibody-conjugated particles were resuspended in PBS diluted 1:6 with sterile filtered $H_2O$ at 1 mg/mL and stored at 4° C. until use.

Figure 10B:
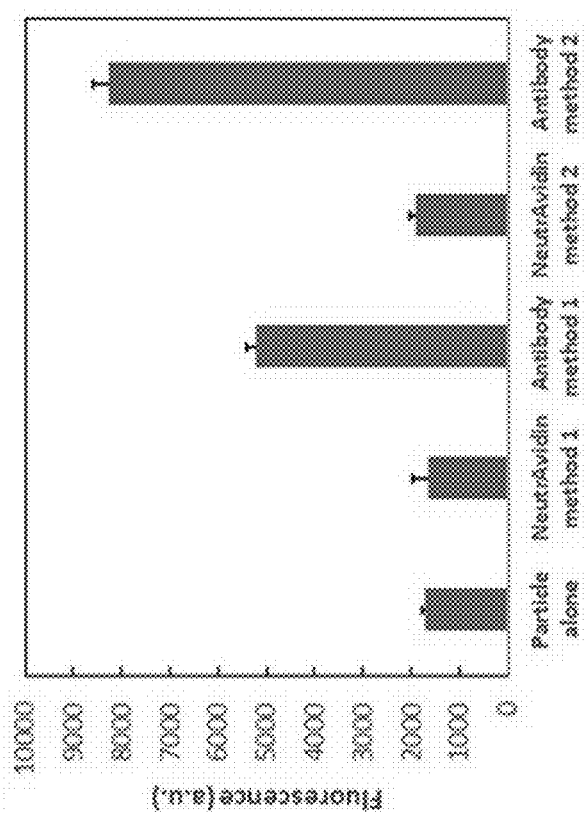
FIGS. 10A and 10B show confirmation of NeutrAvidin and EpCAM antibody conjugation to the Eu-2-amino-BDC particles using the carbodiimide chemistry (method 1) and thiolation chemistry (method 2).
Figure 10A:
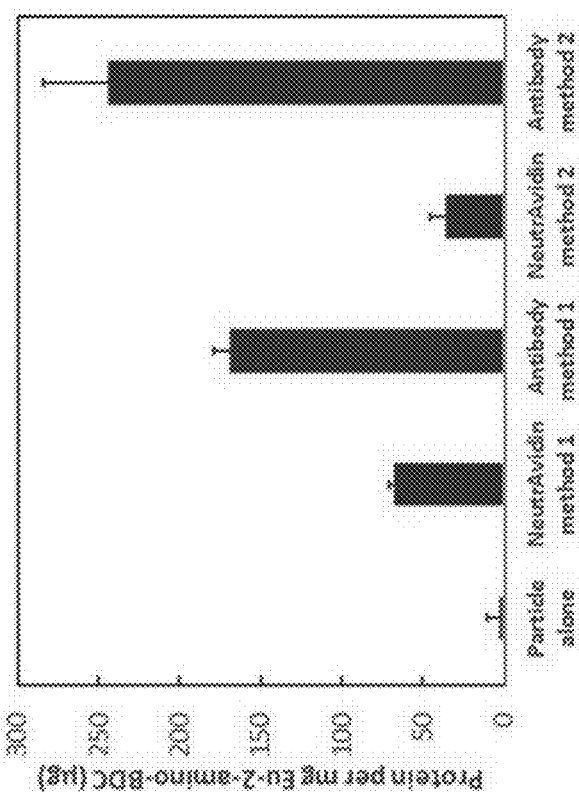

NanoOrange protein quantitation was used to visualize the conjugation of the NeutrAvidin to the Eu-2-amino-BDC particles and the conjugation of the biotinylated EpCAM to the NeutrAvidin, as shown in FIG. 10A. With both conjugation chemistries, there was a significant increase in protein presence between the NeutrAvidin conjugation step and the antibody conugation step. The increase in protein associated with the Eu-2-amino-BDC particles between the NeutrAvidin and antibody steps is indicative of antibody binding.

To confirm that the association of the proteins, either NeutrAvidin or EpCAM antibody, was the result of chemical conjugation rather than association, the Eu-2-amino-BDC particles were incubated with both proteins and protein association was assessed with NanoOrange. The EpCAM antibody alone showed no association with the Eu-2-amino-BDC MOF and both maleimide-activated and un-activated NeutrAvidin demonstrated greater than 3.5-fold reduction in association without chemical conjugation.

To confirm the presence of antibody on the antibody-conjugated Eu-2-amino-BDC particles, a fluorescently labeled secondary antibody was utilized to detect the presence of the EpCAM antibody on the surface of the Eu-2-amino-BDC particles, as shown in FIG. 10B. The Eu-2-amino-BDC particles alone showed the same level of fluorescence as the NeutrAvidin-conjugated particles whereas both the antibody-bound particles showed a significant increase in fluorescence, demonstrating EpCAM antibody binding to the Eu-2-amino-BCD particles.

With both the antibody assay and the protein assay, more antibody is present with the thiolation chemistry. Each NeutrAvidin molecule can bind up to 4 biotinylated antibodies, so the mole ratio of NeutrAvidin to antibody was calculated from the protein assays to determine how many antibodies were bound to NuetrAvidin with each conjugation chemistry. In the case of the carbodiimide chemistry, 1.01 biotinylated antibodies per NeutrAvidin compared to 2.78 antibodies per NeutrAvidin with the thiolation chemistry. In both cases, fewer than the maximal antibodies were attached, likely due to steric hinderance of biotin binding sites due to attachment to a particle surface and density of NeutrAvidin on the surface. However, the carbodiimide chemistry appears to have caused a further decrease in available sites on NeutrAvidin for antibody attachment.

Figure 11:
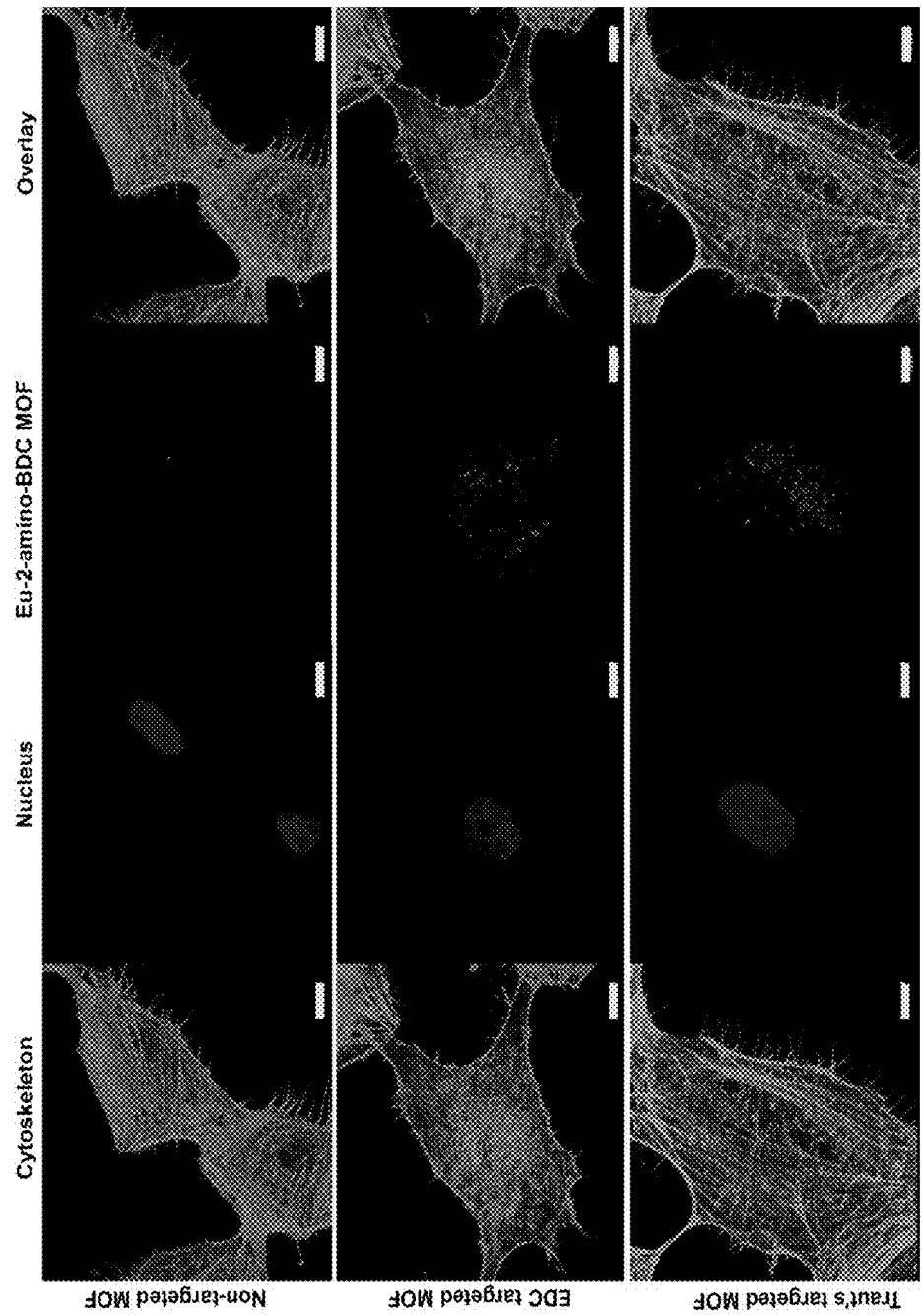
FIG. 11 illustrates MOF interaction with A549 cells. The EpCAM antibody targeted Eu-2-amino-BDC particles showed significant interactions with the EpCAM bearing A549 cells, while the untargeted Eu-2-amino-BDC particles showed minimal interaction after 4 hours. The cell cytoskeleton is visualized using Alexa 488 labeled phalloidin, the nucleus is visualized using DAPI and the Eu-2-amino-BDC particles are visualized using the particle's inherent photoluminescence. Images were collected at 63× and the scale bars represent 10 μm.

Finally, after confirmation of antibody binding to the surface of the Eu-2-amino-BDC particles, the ability of the particles to target human cells bearing the EpCAM antibody on the surface was tested, as shown in FIG. 11. A549 cells were exposed to the antibody-conjugated MOFs for 4 hours, after which time unbound MOFs were washed off the cells. While the untargeted Eu-2-amino-BDC MOFs did show some interaction with the cells, the interaction was minimal, as shown in the upper panel. In contrast, the antibody-conjugated Eu-2-amino-BDC particles showed significant interaction regardless of conjugation methodology, as shown in the lower two panels.

To determine if the antibody targeting Eu-2-amino-BDC particles were internalized, 3D images were created using confocal microscopy. The 3D images were then sliced in the x, y, and z planes to allow clear visualization. With both conjugation methods, the 3D images demonstrated clear internalization into the A549 epithelial cells.

The present invention has been described as a targeted near-infrared imaging with metal-organic frameworks. It will be understood that the above description is merely illustrative of the applications of the principles of the present invention, the scope of which is to be determined by the claims viewed in light of the specification. Other variants and modifications of the invention will be apparent to those of skill in the art.

We claim:

1. A method for targeted near-infrared imaging, comprising:
providing a metal-organic framework, comprising at least one metal cluster comprising six or more rare earth metal ions, wherein the at least one metal cluster comprises a first rare earth metal ion and a second rare earth metal ion that is different from the first rare earth metal ion; and a plurality of carboxylic acid-based linkers coordinating with the at least one metal cluster, wherein the carboxylic acid-based linkers further comprise at least one amine group within the linker; and
conjugating a biological molecule to the metal-organic framework via the at least one amine group within the linker.

2. The method of claim 1, wherein the step of conjugation uses carbodiimide chemistry to react a carboxylic acid group on the biological molecule with an amine group on the metal-organic framework linker to from a carboxamide bond that links the metal-organic framework to the biological molecule.

3. The method of claim 2, wherein the carbodiimide chemistry comprises adding the metal-organic framework to a solution of ethyl(dimethylaminopropyl) carbodiimide.

4. The method of claim 1, further comprising attaching a target molecule to the conjugated biological molecule.

5. The method of claim 4, wherein the conjugated biological molecule comprises streptavidin and the target molecule comprises a biotinylated molecule.

6. The method of claim 1, wherein the conjugated biological molecule comprises an antibody that binds to a target cell.

7. The method of claim 1, wherein the rare earth metal comprises Nd, Yb, Eu, Y, Ce, Pr, Sm, Gd, Tb, Dy, Ho, Er, Tm, or mixtures thereof.

8. The method of claim 1, wherein the carboxylic acid-based linker comprises an amino-containing di-, tri-, tetra-, or hexacarboxylic acid.

9. The method of claim 8, wherein the carboxylic acid-based linker comprises 2-aminoterephthalic acid.

10. A method for targeted near-infrared imaging, comprising:
providing a metal-organic framework, comprising at least one metal cluster comprising one or more rare earth metal ions, and a plurality of carboxylic acid-based linkers coordinating with the at least one metal cluster, wherein the carboxylic acid-based linkers further comprise at least one amine group within the linker; and
conjugating a biological molecule to the metal-organic framework via the at least one amine group within the linker by adding the metal-organic framework to a solution of 2-Iminothiolane to convert an amine group to a sulfhydryl group to provide a thiolated metal-organic framework and reacting the sulfhydryl group of the thiolated metal-organic framework with a sulfhydryl group on the biological molecule to form a disulfide bond that links the metal-organic framework to the biological molecule.

11. A method for targeted near-infrared imaging, comprising:
providing a metal-organic framework, comprising at least one metal cluster comprising one or more rare earth metal ions, and a plurality of carboxylic acid-based linkers coordinating with the at least one metal cluster, wherein the carboxylic acid-based linkers further comprise at least one amine group within the linker; and
conjugating a biological molecule to the metal-organic framework via the at least one amine group within the linker by adding the metal-organic framework to a solution of 2-Iminothiolane to convert an amine group to a sulfhydryl group to provide a thiolated metal-organic framework and reacting the sulfhydryl group of the thiolated metal-organic framework with a maleimide group on the biological molecule to form a thioether bond that links the metal-organic framework to the biological molecule.

12. A method for targeted near-infrared imaging, comprising:
providing a metal-organic framework, comprising at least one metal cluster comprising six or more rare earth metal ions, and a plurality of carboxylic acid-based linkers coordinating with the at least one metal cluster, wherein the carboxylic acid-based linkers further comprise at least one amine group within the linker;
conjugating a biological molecule to the metal-organic framework via the at least one amine group within the linker; and
attaching a target molecule to the conjugated biological molecule, wherein the conjugated biological molecule comprises streptavidin and the target molecule comprises a biotinylated molecule.

* * * * *